United States Patent [19]

Miller

[11] Patent Number: 4,580,944
[45] Date of Patent: Apr. 8, 1986

[54] AERODYNAMIC FLEXIBLE FAIRING

[75] Inventor: Gordon G. Miller, Shelton, Conn.

[73] Assignee: United Technologies Corporation, Hartford, Conn.

[21] Appl. No.: 610,373

[22] Filed: May 15, 1984

[30] Foreign Application Priority Data

May 17, 1983 [JP] Japan .................................. 58-85135
Mar. 23, 1984 [JP] Japan .................................. 59-55377

[51] Int. Cl.⁴ .............................................. B64C 27/33
[52] U.S. Cl. ................................ 416/134 A; 416/224; 416/239; 416/244 R
[58] Field of Search .......... 416/244 D, 245 C, 134 A, 416/239, 61, 138 A, 141, 224, 230 A, 241 A

[56] References Cited

U.S. PATENT DOCUMENTS

| 988,523 | 4/1911 | Toles | 416/245 C X |
|---|---|---|---|
| 2,210,190 | 8/1940 | Stanley | 416/245 C X |
| 2,852,207 | 9/1958 | Jovanovich | 416/88 X |
| 3,008,671 | 11/1961 | Schneiter | 416/245 R |
| 3,331,444 | 7/1967 | Toner | 416/245 C |
| 3,451,644 | 6/1969 | Marchetti et al. | 416/148 X |
| 3,549,444 | 12/1970 | Katz | 416/224 X |
| 3,669,566 | 6/1972 | Bourquardez et al. | 416/140 A X |
| 4,273,511 | 6/1981 | Mouille et al. | 416/141 X |
| 4,403,918 | 9/1983 | Schramm | 416/141 X |
| 4,427,340 | 1/1984 | Metzger et al. | 416/244 D X |

FOREIGN PATENT DOCUMENTS

| 2606424 | 8/1977 | Fed. Rep. of Germany | 416/245 C |
|---|---|---|---|
| 931198 | 2/1948 | France | 416/102 |
| 972677 | 8/1950 | France | 416/102 |

Primary Examiner—Everette A. Powell, Jr.
Attorney, Agent, or Firm—Alan C. Cohen

[57] ABSTRACT

The present invention is a flexible fairing for covering rotor connections on a rotor wing aircraft. Such a fairing would comprise a flexible polyurethane foam material which could maintain its aerodynamic shape while in flight yet be compliant enough to allow for changes in blade pitch without adding significant torsional stiffness to the connector. In addition, a flexible urethane rubber coating may be used to protect the foam fairing for abrasion or moisture absorption.

4 Claims, 1 Drawing Figure

U.S. Patent  Apr. 8, 1986  4,580,944
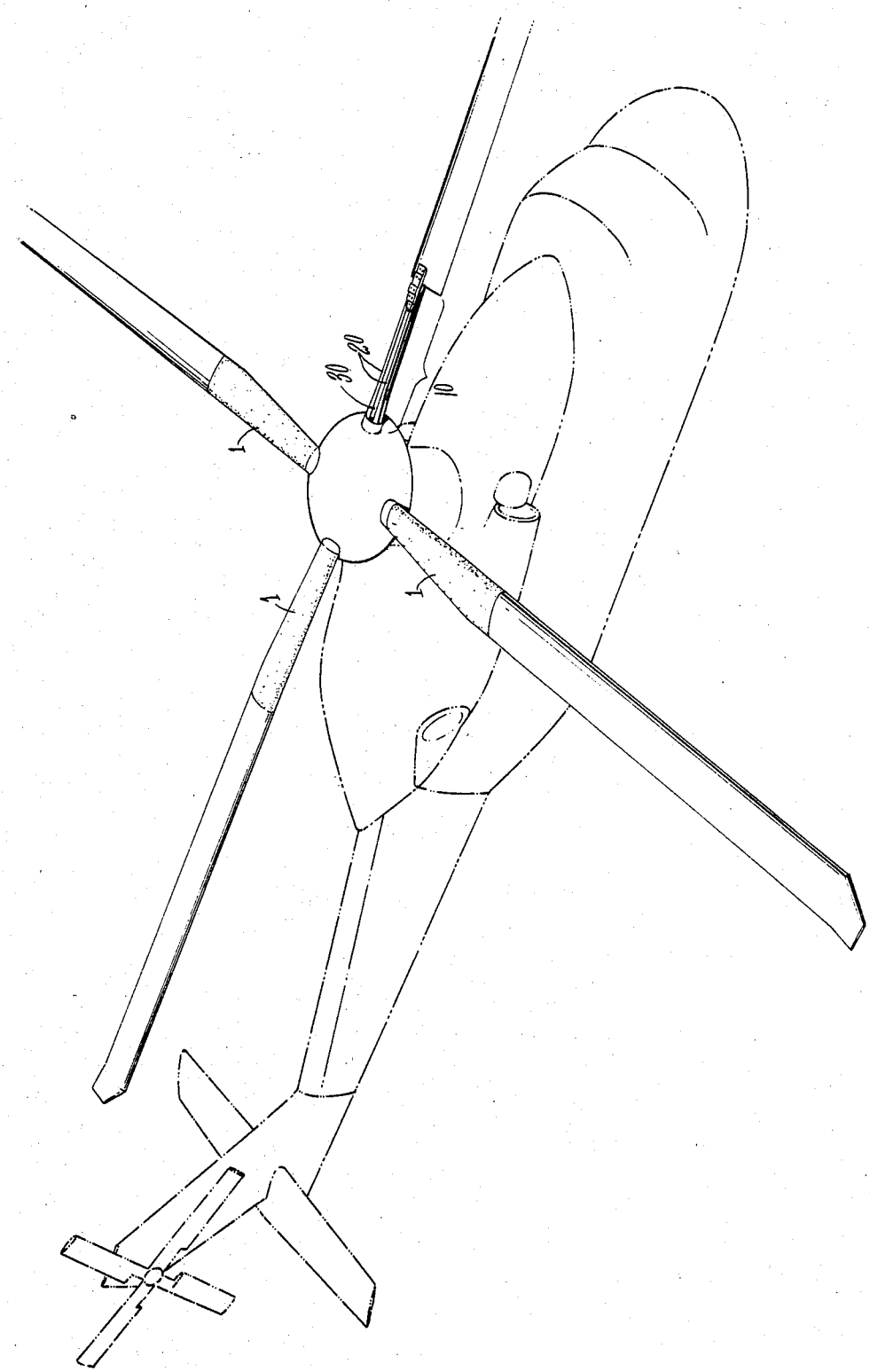

AERODYNAMIC FLEXIBLE FAIRING

TECHNICAL FIELD

The present invention relates to aerodynamic structures and in particular fairings.

BACKGROUND ART

A recent development in rotor hub design for rotary wing aircraft has introduced a rotor connector in place of the torque tube. Typically, the rotor connector contains one or more structural members, a pitch shaft and a push rod assembly. The inboard end of this assembly is fixed to the main rotor hub by a spherical bearing mounted to fix the center of pitch rotation and react the push rod load in shear. While the outboard portion attaches to the rotor blade. Through the operation of the push rod and pitch shaft, it is possible to alter the pitch of the rotor blade to conform to a particular flight mode. This may be done by applying torque to the inboard portion of the pitch shaft via the push rod rotating or twisting the pitch shaft such that it changes the pitch of the rotor blade connected at the outboard end of the pitch shaft.

Rotor connectors of this type are about 3 to about 5 feet in length and since they are not aerodynamic in design, they generate aerodynamic drag when in use. In addition, if they are not covered, they are subject to attack by foreign objects and erosion by the elements. In the past, when a structure was non-aerodynamic, a rigid aerodynamic fairing would be used to both protect the structure as well as to conform into an aerodynamic shape, thus producing additional lift. However, such a rigid structure would not be able to withstand the bending and twisting motions associated with these novel rotor connectors. Therefore, what is needed in the art is a flexible compliant fairing which is capable of maintaining its aerodynamic shape in flight and will not lose its structural integrity when subjected to the twisting forces associated with the changes in blade pitch.

DISCLOSURE OF INVENTION

The present invention is for a flexible fairing which is useful in forming an aerodynamic form about the rotor connectors. Said fairings may be formed of flexible urethane foam which will hold its shape when under centrifugal and aerodynamic loading. The urethane foam fairing should add no significant increase in stiffness in either bending or torsion of the flex beams when the blade pitch is changed. In addition, the fairing may include a flexible urethane coating to protect the foam fairing from abrasion, moisture absorption and other contamination.

Other features and advantages will be apparent from the specification and claims and from the accompanying drawings which illustrate an embodiment of the invention.

BRIEF DESCRIPTION OF DRAWINGS

The drawing illustrates a flexible fairing of the present invention.

BEST MODE FOR CARRYING OUT THE INVENTION

The foam which may be used to practice this invention may be any flexible urethane foam that is capable of being formed into an aerodynamic shape and will substantially retain its shape under the forces produced in flight and blade pitch changes. The foam should have good moisture resistance and be compliant enough to allow the outboard end to rotate through a pitch change of up to about $\pm 30°$ to the normal axis without cracking or significantly contributing to the torsional stiffness of the rotor connector. A significant increase in the stiffness may result in higher pitch rod or control loads which could lead to undesirable handling qualities of the aircraft. In addition, such increased stiffness may require the use of heavier, stronger components due to the higher stresses resulting in a less desirable product.

The particular polyurethane foam which is used will depend upon the particular stresses and torsional stiffnesses desired for a particular aircraft. It is apparent that a larger rotor connector which required larger structural members having inherent in it a higher torsional stiffness could accommodate a less compliant polyurethane fairing. Typical polyurethane foams which may be used to practice this invention are available in several densities, i.e. 3 lbs. per cubic ft., 6 lbs. per cubic ft., 10 lbs. per cubic ft., etc. These foams are typically two component systems, A and B, wherein part A is the urethane base material and part B is the catalyst. The particular foam selected should also not deteriorate (crack, crumble, become brittle, etc.) when operating at temperatures of from about $-65°$ F. ($-47.8°$ C.) to about $150°$ F. ($65.5°$ C.).

These foams are typically closed cell and are characterized by compression-deflection data. It is believed that any urethane foam system which, when processed, will result in a compressive-modulus of foam about 50 to about 175 psi will result in an acceptable fairing. However, it should be pointed out that the particular rotor system will determine the particular foam requirements.

Some foam systems which may be used are listed in the table.

Any of the conventional techniques which may be used to form the fairing, i.e. injection molding directly over the rotor connector superstructure or forming the fairing in two or more sections and fitting them about the rotor connector may be used. It should be pointed out that in the injection molding technique, it may be desirable to protect the area between the pitch shaft and the flex beam from invasion by the foam which may increase the apparent torsional stiffness of the connector. However, the foam may be permitted to encompass the pitch shaft providing that it does not bond to the shaft and a low friction (Teflon type) surface is placed between them. In the alternative, a clearance around the pitch shaft may be necessary to permit freedom of motion of the pitch shaft during flight, or under dynamic loads.

Due to the susceptibility of the polyurethane foam to moisture damage and abrasion, an abrasion and moisture resistant polyurethane rubber coating is recommended. This may be done by applying the rubber in the form of a liquid or using the rubber in sheet form. The particular urethane rubber should have substantially the same flexible qualities as the foam so that when the rotor pitch is altered and the fairing twists, the abrasion coating does not separate from the foam. Although it is believed that a number of urethane rubbers may be used, one such material is PR 1592, a liquid rubber available from Products Research & Chemical Corporation. This material may be applied directly onto the foam fairing by brushing, squeegeeing, etc. in the liquid form or it may be cast into sheet form and then attached to the foam with an adhesive. It may also be possible, when using rubber sheet stock, to co-cure the foam and the rubber coating together. This may be done by lining the mold with the rubber sheet stock and then injecting the foam into the lined mold forming a complete fairing in one curing step.

The FIGURE illustrates a flexible fairing 1 which is shaped about the rotor connector 10 which comprises two flexbeams 20 and a pitch shaft 30.

It is believed that the novel fairing disclosed herein results in an aerodynamic, protective cover for rotor connectors. The fairing will not only add additional aerodynamic lift to the aircraft, but it will also protect it from erosion by the elements or foreign object damage which could seriously damage the aircraft and possibly cause the aircraft to crash.

I claim:

1. In a rotary wing aircraft having a flexible rotor connector comprising one or more flexbeams, a pitch shaft and a means for applying torque to the shaft to alter the pitch of the rotor wherein said flexbeams and pitch shaft are enclosed in a torsionally compliant, aerodynamic fairing which is capable of maintaining an aerodynamic shape during flight, protect the enclosed flexbeams and pitch shaft from damage due to debris while being sufficiently compliant to allow the outboard end to rotate through a pitch change of up to about +30 degrees to the normal axis without cracking or significantly contributing to the torsional stiffness of the rotor connector.

2. The article of claim 1 wherein the compliant fairing is formed of a urethane foam.

3. The article of claim 1 wherein the compliant urethane foam has a compressive modulus of about 50 psi to about 175 psi.

4. The article of claim 1 wherein the compliant fairing has an outer coating of an erosion resistant polyurethane rubber.

* * * * *